United States Patent [19]

Elsheikh

[11] Patent Number: 4,962,244
[45] Date of Patent: Oct. 9, 1990

[54] PROCESS FOR PRODUCING 1,1-DICHLORO-1-FLUOROETHANE AND/OR 1-CHLORO-1,1-DIFLUOROETHANE FREE OF VINYLIDENE CHLORIDE

[75] Inventor: Maher Y. Elsheikh, Tredyffrin, Pa.

[73] Assignee: Atochem North America, Inc., Philadelphia, Pa.

[21] Appl. No.: 332,690

[22] Filed: Apr. 3, 1989

[51] Int. Cl.$^5$ ............................................. C07C 17/00
[52] U.S. Cl. ...................................................... 570/165
[58] Field of Search ........................................... 570/165

[56] References Cited

U.S. PATENT DOCUMENTS 2,894,676  7/1959  Prill.
3,833,676  9/1974  Ukaji et al. ..................... 260/653.7
4,849,555  7/1989  Cheminal ......................... 510/165

OTHER PUBLICATIONS

Gutsche Fundamentals of Org. Chem. (1975), p. 182.
Chem. Abstract 93:185661c (1981), abstracting Grigor-'év et al., Izv. Akad. Nauk. SSR, Ser. Khim., 6, 1333–1336 (1980).
Henne et al., J. Am. Chem. Soc., 70, 758–760 (1945).

Primary Examiner—Alan Siegel
Attorney, Agent, or Firm—Seidel, Conda, Lavorgna & Monaco

[57] ABSTRACT

1,1-Dichloro-1-fluoroethane and 1-chloro-1,1-difluoroethane are prepared from the liquid phase fluorination of 1,1,1-trichloroethane by HF in the presence of a homogenous catalyst. 1,1-Dichloro-1-fluoroethane or 1-chloro-1,1-difluoroethane are selectively produced substantially free of vinylidene chloride.

11 Claims, No Drawings

PROCESS FOR PRODUCING 1,1-DICHLORO-1-FLUOROETHANE AND/OR 1-CHLORO-1,1-DIFLUOROETHANE FREE OF VINYLIDENE CHLORIDE

FIELD OF THE INVENTION

The present invention relates to the manufacture of 1,1-dichloro-1-fluoroethane and/or 1-chloro-1,1-difluoroethane by fluorination of 1,1,1-trichloroethane. More particularly, it relates to a liquid phase process for the fluorination of 1,1,1-trichloroethane with hydrogen fluoride to selectively produce 1,1-dichloro-1-fluoroethane or 1-chloro-1,1-difluoroethane free of contaminating vinylidene chloride, or other by product, such as 2,2,4,4-pentafluorobutane.

BACKGROUND OF THE INVENTION

1,I-Dichloro-1-fluoroethane is presently under consideration as a replacement for trichlorofluoromethane as a foam blowing agent. It has a substantially lower ozone depletion index than trichlorofluoromethane. Moreover, 1,I-dichloro-1-fluoroethane displays a 10-15% greater blowing efficiency in rigid foam, and improved solubility in aromatic polyester polyol, in comparison to trichlorofluoromethane.

In the manufacture of 1,1-dichloro-1-fluoroethane and 1-chloro-1,1-difluoroethane, by-products are generated. 1,1,1-Trichloroethane is susceptible to dehydrohalogenation, which leads to the formation of vinylidene chloride. The latter is a particularly undesirable by-product, since it is a suspected carcinogen. Vinylidene chloride and 1,1-dichloro-1-fluoroethane boil at 31° C. and 32° C., respectively. Thus, they cannot be readily separated by distillation.

2,2,4,4-Pentafluorobutane is another undesirable by-product of the fluorination of 1,1,1-trichloroethane. I believe that it is formed by the reaction between 1,1,1-trichloroethane and vinylidene chloride, followed by the reaction of additional 1,1,1-trichloroethane with vinylidene chloride to give 1,1,1,3,3-pentachlorobutane. Grigor'ev et al., Izv. Akad. Nauk. SSSR. Ser. Khim., 6, 1333-6 (1980). Hydrofluorination of the latter produces 2,2,4,4-pentafluorobutane.

2,2,4,4-Pentafluorobutane is the principle organic component of reactor bottoms or "tars" which are typically generated in the fluorination of 1,1,1-trichloroethane, particularly at high temperatures. The build-up of tar substances as reactor bottoms effectively slows the production rate to a point where the reaction mixture must be dumped.

Several approaches have been developed to eliminate the co-production of tars and/or vinylidene chloride in the fluorination of 1,1,1-trichloroethane.

U.S. Pat. No.2,894,044 discloses the vapor phase fluorination of 1,1,1-trichloroethane to 1,1-dichloro-1-fluoroethane by hydrogen fluoride over a catalyst selected from the group of stannic fluoride on activated carbon and aluminum fluoride. The patentee states that under certain conditions these catalysts cause fluorination of I,1,1-trichloroethane without appreciable dehydrohalogenation. Despite this statement, the examples of U.S. Pat. No. 2,894,044, evidence substantial co-production of vinylidene chloride.

U.S. Pat. No. 3,833,676 discloses a non-catalytic process for the fluorination of 1,1,1-trichloroethane to give 1,1-dichloro-1-fluoroethane and 1-chloro-1,1-difluoroethane. However, the process requires a molar ratio of hydrogen fluoride to 1,1,1-trichloroethane of at least 4:1. The process has little selectivity for 1,1-dichloro-1-fluoroethane.

Henne et al., J. Am. Chem. Soc., 70, 758–60 (1945) reported that the addition of hydrogen fluoride to olefins in the liquid phase may be accelerated in the presence of boron trifluoride. The reaction was characterized by low conversion, and polymer formation. Despite this teaching, it has not been heretofore known that the fluorination of 1,1,1-trichloroethane to selectively produce 1,1-dichloro-1-fluoroethane substantially free of vinylidene chloride and polymer formation, may be carried out.

SUMMARY OF THE INVENTION

A process for the preparation of 1,1-dichloro-1-fluoroethane and/or 1-chloro-1,1-difluoroethane substantially free of vinylidene chloride is provided. 1,1,1-Trichloroethane is treated with anhydrous hydrogen fluoride in the liquid phase in a molar ratio of hydrogen fluoride to 1,l,I-trichloroethane of from about 10:1 to about 1:1, at a temperature of from about 22° C. to about 200° C., in the presence of from about 0.1 mole % to about 10 mole % of a homogenous Lewis acid catalyst, based upon the combined amount of the catalyst and hydrogen fluoride.

DETAILED DESCRIPTION OF THE INVENTION

We have found that hydrogen fluoride readily adds to vinylidene chloride to form 1,1-dichloro-1-fluoroethane in the presence of a homogenous Lewis acid catalyst, preferably boron trifluoride. The reaction provides 98% conversion of vinylidene chloride with as high as 97% selectively for the product, 1,1-dichloro-1-fluoroethane, at relatively low temperatures and atmospheric pressure. The inclusion of a catalytic amount of a homogenous catalyst in the 1,1,1-trichloroethane reaction mixture ensures that any vinylidene chloride which may be generated by dehydrohalogenation of 1,1,1-trichloroethane is quickly converted to 1,1-dichloro-1-fluoroethane. Additional processing to separate vinylidene chloride from the product is obviated. The product is substantially free of vinylidene chloride. By "substantially free of vinylidene chloride" is meant that the product, on a mole percent basis, contains no more than about 0.2 percent vinylidene chloride.

Preferably, the product contains no more than about 0.05 mole percent vinylidene chloride, and most preferably contains essentially zero vinylidene chloride, based upon the limits of analysis.

In accelerating the conversion of any vinylidene chloride generated to 1,1-dichloro-1-fluoroethane, it is believed that formation of the undesirable by-product 2,2,4,4-pentafluorobutane is avoided. Without wishing to be bound by any theory, it is believed that the catalyzed fluorination of vinylidene chloride to 1,1-dichloro-1-fluoroethane in the reaction mixture proceeds preferentially over the addition of 1,1,1-trichloroethane to vinylidene chloride by C-Cl insertion to form the 2,2,4,4,4-pentafluorobutane precursor 1,1,1,3,3-pentachlorobutane. Thus, the reaction provides for the production of 1,1-dichloro-1-fluoroethane and 1-chloro-1,1-difluoroethane from the hydrofluorination of 1,1,1-trichloroethane without coproduction of 2,2,4,4-pentafluorobutane and other tar substances.

According to the present invention, the fluorination of 1,1,1-trichloroethane is effected by treating 1,1,1-trichloroethane with anhydrous hydrogen fluoride in the liquid phase, in the presence of a homogenous Lewis acid catalyst. The amount of catalyst required depends upon the reaction conditions and the nature of the catalyst. The catalyst is generally present in the amount of from about 0.1 to about 10 mole percent, based upon the combined amounts of catalyst and hydrogen fluoride in the reaction mixture. The catalyst amount is advantageously selected between these limits to achieve conversion of 1,1,1 trichloroethane without generating vinylidene chloride.

Suitable catalysts include, for example boron trifluoride. Other suitable catalysts include the salts of the following species, particularly the chlorides thereof: tin (IV), antimony (V), bismuth (III) and arsenic (III). These catalysts are effectively converted to their corresponding metal fluorides in the presence of hydrogen fluoride. The catalyst is of the homogenous type, that is, it is substantially soluble in the liquid reaction mixture. The reactants and the catalyst form essentially a single liquid phase, as contrasted to heterogenous catalysis wherein the reactants and catalyst comprise separate phases. Vapor phase hydrofluorination of 1,1,1-trifluoroethane in the presence of heterogenous catalysts has been observed to lead to substantial co-production of vinylidene chloride as in, for instance, U.S. Pat. No. 2,899,044.

The term "Lewis acid" is used herein according to its ordinary meaning. A Lewis acid is generally defined as any molecule or ion capable of forming a covalent bond with two electrons from a second molecule or ion. A Lewis acid is thus an electron acceptor. The term "Lewis acid catalyst" as used herein includes not only those species suitable for catalyzing hydrofluorination of hydrochlorocarbons, which species comprise Lewis acids per se, but also includes catalytic species which, while not Lewis acids per se, are readily converted to Lewis acids under the conditions utilized herein. An example of such a catalyst is $B_2O_3$. Some Lewis acids, which nevertheless are only weakly acidic, may be utilized in the practice of the invention provided they are converted to more active species in the presence of hydrogen fluoride. An example of such a weak Lewis acid is $B(OH)_3$. In the presence of hydrogen fluoride, it is readily converted to the corresponding strongly acidic Lewis acid, boron trifluoride.

Boron trifluoride is particularly useful in the practice of the invention. It may be introduced into the reaction mixture in a vapor state. Upon contact with hydrogen fluoride, boron trifluoride reacts to form liquid tetrafluoroboric acid as the catalytic species.

Preferably, the catalyst is present in the amount of from about to about 3 mole percent, based upon the combined amount of catalyst and hydrogen fluoride.

The molar ratio of hydrogen fluoride to 1,1,1-trichloroethane in the reaction mixture can vary from about 10:1 to about 1:1. The ratio is preferably from about 3:1 to about 1:1.

The reaction temperature ranges generally from about room temperature, i.e., about 22° C., to about 200° C. Preferably the temperature ranges from about 22° C. to about 100° C., most preferably from about 22° C. to about 75° C.

The reaction is carried out in the liquid phase under autogenous pressure, in any suitable reaction vessel. Such vessels are known to those skilled in the art.

The reaction time should be sufficient to fluorinate a substantial quantity of 1,1,1-trichloroethane to 1,1-dichloro-1-fluoroethane, which may be further reacted to produce 1-chloro-1,1-difluoroethane. Reaction times of 2 hours or more may be generally used. It should be appreciated by those skilled in the art that shorter reaction times may be utilized by the expedient of simply increasing the reaction temperature. The reaction time may vary to some extent with the feed ratio of hydrogen fluoride to 1,1,1-trichloroethane.

While the fluorination reaction of the present invention is most conveniently conducted at autogenous pressure, higher or lower pressures may be utilized.

The invention is useful for producing either 1,1-dichloro-1-fluoroethane or 1-chloro-1,1-difluoroethane selectively, with a high level of conversion of 1,1,1-trichloroethane. The desired product may be obtained by varying the temperature, reaction time, catalyst concentration, or any combination thereof. Generally, production of 1,1-dichloro-1-fluoroethane over 1-chloro-1,1-difluoroethane is favored at lower temperatures, shorter reaction times and lower catalyst ion concentrations. The molar ratio of hydrogen fluoride to 1,1,1-trifluoroethane may also influence product selectively, with an increasing excess of hydrogen fluoride generally favoring formation of the more fluorinated product, 1-chloro-1,1-difluoroethane.

According to one aspect, the invention comprises a process for the production of 1,1-dichloro-1-fluoroethane as the dominant product, that is, the hydrofluorination product comprises, on a mole percent basis, at least about 50% 1,1-dichloro-1-fluoroethane. By selecting the appropriate conditions, the manipulation of which will be readily attainable by those skilled in the art, product selectivities for 1,1-dichloro-1-fluoroethane may be increased to 90 mole %, 95 mole %, or even as high as about 97 mole%.

The practice of the invention is illustrated by the following non-limiting examples, utilizing a 3.3:1 molar ratio of hydrogen fluoride to 1,1,1-trichloroethane. The reaction was conducted in the presence of zero (Example 2), 1.4 (Examples 1–3) or 2.4 (Example 5) mole percent boron trifluoride catalyst, based upon the combined amount of boron trifluoride and hydrogen fluoride in the reaction mixture.

EXAMPLE 1

To a 600 ml capacity stainless steel reactor fitted with a magnetic stirrer, $BF_3$ gas inlet, HF gas inlet, pressure gauge and product outlet, was added 100 grams of 1,1,1-trichloroethane, followed by 50 grams of hydrogen fluoride and 2.5 grams of boron trifluoride. The mixture was stirred for 2.5 hours at 60° C. and 95 psi, and the gaseous products were vented from the top of the reactor through a valve, and admitted to the bottom of a scrubbing tower packed with a polyethylene packing material. The acid contents of the product mixture were neutralized with 1-5N potassium hydroxide solution, which was fed from the top of the scrubbing tower by means of a feed pump. The caustic solution was circulated back into a potassium hydroxide reservoir. The gaseous product was then dried in a drying tower packed with anhydrous calcium sulfate. A portion of the dry gas product was diverted to a gas chromatograph, through a sampling valve. The remaining gaseous product was cooled down using an ice bath, and HF was extracted by adding ice cold water. The organic layer was then separated from the cold mixture using a separatory funnel, and subsequently dried over anhydrous calcium sulfate, followed by gas chromatograph analysis. The extent of 1,1,1-trichloroethane conversion to product was estimated from the amount of unreacted 1,1,1-trichloroethane contained in the product. Under the conditions of the reaction, 60% conversion of 1,1,1-trichloroethane to product (97.3 mole % 1,1-dichloro-1-fluoroethane; 2.4 mole % 1-chloro-1,1-difluoroethane), was observed with no 1,1,1-trifluoroethane or vinylidene chloride being formed.

EXAMPLE 2

Example 1 was repeated except that the temperature was raised from 60° C. to 70° C., which caused the reaction pressure to increase from 95 psi to 111 psi. A 77% conversion of 1,1,1-trichloroethane was achieved. No vinylidene chloride was detected in the product. The selectivity for 1,1-dichloro-1-fluoroethane was 81.1 mole %. The selectivity for 1-chloro-1,1-difluoroethane was 18.9 mole %.

EXAMPLE 3

Example was repeated, increasing the reaction temperature to 75° C. The pressure increased to 160 psi. A 98.1% conversion of 1,1,1-trichloroethane was achieved. No vinylidene chloride was formed. The selectivity for 1,1-dichloro-1-fluoroethane was 67.51 mole %. The selectivity for 1-chloro-1,1-difluoroethane was 32.5 mole %.

EXAMPLE 4

The procedure of Example 2 was repeated, except that the boron trifluoride catalyst was omitted. Only 20% of the 1,1,1-trichloroethane was converted to product. Moreover, in the absence of boron trifluoride, the product mixture was observed to contain 1 mole % vinylidene chloride. The selectivities for 1,1-dichloro-1-fluoroethane and 1-chloro-1,1-difluoroethane were 94.5 mole % and 4.5 mole %, respectively.

EXAMPLE 5

Example 2 was repeated except that the amount of boron trifluoride catalyst was increased from 2.5 grams to 4.0 grams. The reaction pressure was observed to increase to 240 psi. An 84% conversion of 1,1,1-trichloroethane was achieved. No vinylidene chloride was detected. The product selectivities were 58.4 mole % for 1,1-dichloro-1-fluoroethane, 40.2 mole % for 1-chloro-1,1-difluoroethane and 1.4 mole % for 1,1,1-trifluoroethane.

The data from the preceding examples is summarized in the following Table.

| Example | REACTION MIXTURE (grams) | | | T(°C.) | P(psi) | $CH_3CCl_3$ Conversion (mole %) | Reaction Time(hrs) | PRODUCT DISTRIBUTION (mole %) | | | |
|---|---|---|---|---|---|---|---|---|---|---|---|
| | $CH_3CCl_3$ | HF | $BF_3$ | | | | | $CH_3CCl_2F$ | $CH_3CClF_2$ | $CH_3CF_3$ | $CH_2=CCl_2$ |
| 1 | 100 | 50 | 2.5 | 60. | 95 | 60 | 2.5 | 97.3 | 2.4 | 0 | 0 |
| 2 | 100 | 50 | 2.5 | 70. | 111 | 77 | 2.5 | 81.1 | 18.9 | 0 | 0 |
| 3 | 100 | 50 | 2.5 | 75. | 160 | 98.1 | 2.5 | 67.5 | 32.5 | 0 | 0 |
| 4 | 100 | 50 | 0 | 70. | 118 | 20 | 2.5 | 94.5 | 4.5 | 0 | 1 |
| 5 | 100 | 50 | 4.0 | 70. | 240 | 84 | 2.5 | 58.4 | 40.2 | 1.4 | 0 |

The data indicates that using a 3.3:1 molar ratio of hydrogen fluoride to 1,1,1-trichloroethane, in the presence of 1.4 mole % boron trifluoride, based upon the combined amounts of hydrogen fluoride and boron trifluoride, results in 60% conversion of 1,1,1-trichloroethane at 60° C., with 97.3% selectivity for 1,1-dichloro-1-fluoroethane. At 75° C., conversion increased to 98.1%, while selectivity for 1,1-dichloro-1-fluoroethane was still 67.5%, with the only by-product being 1-chloro-1,1-difluoroethane. Vinylidene chloride was not a by-product at either 60° C. or 75° C. In the absence of the catalyst, however, conversion of 1,1,1-trichloroethane was only 20% at 70° C., and the product contained 1 mole % vinylidene chloride. Increasing the concentration of boron trifluoride to 2.4 mole % increased the rate of conversion of 1,1,1-trichloroethane to 84%, while selectivity for 1,1-dichloro-1-fluoroethane decreased to 58.4%. No vinylidene chloride was produced.

The present invention may be embodied in other specific forms without departing from the spirit or essential attributes thereof and, accordingly, reference should be made to the appended claims, rather than to the foregoing specifications, as indicating the scope of the invention.

What is claimed is:

1. A process for forming 1,1-dichloro-1-fluoroethane and/or 1-chloro-1,1-difluoroethane substantially free of vinylidene chloride comprising treating 1,1,1-trichloroethane with anhydrous hydrogen fluoride in the liquid phase in a molar ratio of hydrogen fluoride to 1,1,1-trichloroethane of from about 10:1 to about 1:1, at a temperature of from about 22° C. to about 200° C., in the presence of from about 0.1 mole % to about 10 mole % of a boron containing catalyst, based upon the combined amount of the catalyst and hydrogen fluoride, said catalyst consisting essentially of boron trifluoride or a compound which is converted to boron trifluoride under the reaction conditions of said process.

2. A process according to claim 1 wherein the mole ratio of hydrogen fluoride to 1,1,1-trichloroethane is from about 3:1 to about 1:1.

3. A process according to claim 1 wherein the catalyst is present in the amount of from about 1 mole % to about 3 mole %, based upon the combined amount of catalyst and hydrogen fluoride.

4. A process according to claim 1 wherein the reaction temperature is from about 22° C. to about 100° C.

5. A process according to claim 4 wherein the reaction temperature is from about 22° C. to about 75° C.

6. A process according to claim 1 wherein the molar ratio of hydrogen fluoride to 1,1,1-trichloroethane is from about 3:1 to about 1:1, the catalyst is present in the amount of from about 1 mole % to about 3 mole %, based upon the combined amount of catalyst and hydrogen fluoride, and the reaction temperature is from about 22° C. to about 100° C.

7. A process according to claim 6 wherein the temperature is from about 22° C. to about 75° C.

8. A process according to claim 1 wherein the product comprises, on a mole percent basis, at least about 50% 1,1-dichloro-1-fluoroethane.

9. A process according to claim 1 wherein the product comprises, on a mole percent basis, at least about 90% 1,1-dichloro-fluoroethane.

10. A process according to claim 1 wherein the catalyst is boron trifluoride.

11. A process according to claim 6, wherein the catalyst is boron trifluoride.

* * * * *

UNITED STATES PATENT AND TRADEMARK OFFICE
CERTIFICATE OF CORRECTION

PATENT NO. : 4,962,244

DATED : October 9, 1990

INVENTOR(S) : Maher Y. Elsheikh

It is certified that error appears in the above-identified patent and that said Letters Patent is hereby corrected as shown below:

Column 5, line 23, insert --1-- after "Example"; Claim 1, column 6, line 26, delete "boron containing" and insert --homogeneous--; Claim 9, column 6, line 64, change "1,1-dichloro-fluoroethane" to --1,1-dichloro-1-fluoroethane--.

Signed and Sealed this

Twenty-fifth Day of February, 1992

Attest:

HARRY F. MANBECK, JR.

*Attesting Officer*     *Commissioner of Patents and Trademarks*